United States Patent [19]

McWhorter et al.

[11] Patent Number: 5,158,081
[45] Date of Patent: Oct. 27, 1992

[54] METHOD FOR TREATMENT OF SOFT TISSUE WOUNDS BY ELECTRICAL STIMULATION

[75] Inventors: Luther S. McWhorter; Mark H. Chandler, both of Pinehurst, N.C.

[73] Assignee: Trillion Medical Resources, Inc., Pinehurst, N.C.

[21] Appl. No.: 707,062

[22] Filed: May 29, 1991

[51] Int. Cl.⁵ .......................... A61N 1/18; A61N 1/30
[52] U.S. Cl. ................................... 128/421; 128/800; 604/20
[58] Field of Search .............. 128/421–422, 128/419 R, 801–802; 604/20

[56] References Cited

U.S. PATENT DOCUMENTS

| | | | |
|---|---|---|---|
| 4,211,222 | 7/1980 | Tapper | 604/20 |
| 4,301,794 | 10/1981 | Tapper | 604/20 |
| 4,340,047 | 7/1982 | Tapper | 604/20 |
| 4,727,878 | 3/1988 | Levine | 128/421 |
| 4,738,250 | 4/1988 | Fulkerson et al. | 128/421 |
| 4,764,164 | 8/1988 | Sasaki | 604/20 |
| 4,846,181 | 7/1989 | Miller | 128/421 |
| 4,895,154 | 1/1990 | Bartelt et al. | 129/421 |
| 4,982,742 | 1/1991 | Claude | 128/422 |
| 5,047,007 | 9/1991 | McNichols et al. | 128/421 |
| 5,058,605 | 10/1991 | Slovak | 128/421 |

OTHER PUBLICATIONS

L. Wolcott et al., "Accelerated Healing of Skin Ulcers by Electrotherapy", Southern Med. Journal, pp. 795–801, 1969.

Assimacopoulos, D., "Wound Healing Promotion by the Use of Negative Electric Current", Am. J. Surg., pp. 423–431, 1968 (No. 6).

Gault, Walter, "Use of Low Intensity Direct Current in Management of Ischemic Skin Ulcers", Physical Therapy, pp. 265–269, vol. 56/#3, Mar. '76.

Carley, P. J. et al., "Electrotherapy for Acceleration of Wound Healing: Low Intensity Direct Current", Arch. Phys. Med. Rehabil, vol. 66, Jul. 1985.

*Primary Examiner*—Lee S. Cohen
*Assistant Examiner*—J. Jastrzab
*Attorney, Agent, or Firm*—Rhodes, Coats & Bennett

[57] ABSTRACT

A method for treating pressure sores, decubitus ulcers, or other soft tissue wounds involves the application of a pulsed DC current to the patient's body to stimulate healing of the soft tissue wound. In accordance with the present invention, a pair of electrodes are applied to the patient's body outside the area of the sore, but closely adjacent the outer edges of the sore. The electrodes are placed on opposite sides of the sore and a current is applied to the patient's skin through the electrodes so that the current path is across the sore. The current is applied for a short duration and the probes are repositioned. The process is repeated as many times as necessary to direct current across the entire surface area of the wound. Unlike prior art methods of electrotherapy, the method of the present invention takes only a few minutes to treat each sore.

18 Claims, 4 Drawing Sheets

METHOD FOR TREATMENT OF SOFT TISSUE WOUNDS BY ELECTRICAL STIMULATION

TABLE 1
CLINICAL STUDIES

| Journal/ Investigator | Number Patients | Type & Number of Ulcers | Type of Treatment | Hrs. of Total Treatment Time/Wk. | Avg. # of Wks. Req. for Healing | Healing Rate Per Wk. |
|---|---|---|---|---|---|---|
| Assimacopoulos (1968) Am. J. Surg. | 3 | 6 (venous stasis) | low intensity DC (75-100 microamp) | 168 | 4.4 | |
| Wolcott et. al. (1969) Southern Med. J. | 67 | 8:control 75:treatment (Ischemic ulcers) | low intensity DC (approx 600 microamp) | 42 | 9.5 | 13.4%/wk healing rate vs. 5% per week for controls |
| Gault & Gatens (1976) Phys. Ther. | 76 | 6:control 100:treatment (Ischemic ulcers) | low intensity DC (200-1000 microamp) | 42 | 4.7 | 30%/wk healing rate vs. 14.7%/wk for controls |
| Cartey & Wainapel (1975) Arch. Phys. Med. | 30 | 15:control 15:treatment (Indolent ulcers) | low intensity DC (300-700 microamp) | 20 | 5 | 17.9%/wk healing rate vs. 9%/wk for controls |
| Barron, et. al. (1985) Minn. Med. | 6 | 6 decubitus ulcers (resisted treatment up to 1 yr.) | Biphasic pulses 600 microamp at 0.5 Hz w/electronic waveform control | 3 | 4 | |
| Alon, et. al. (1986) Phys. Ther. | 15 | 15 diabetic ulcers (persisted for avg. 8.6 mos.) | high voltage short duration pulses (80 Hz) | 3 | 11.3 | |
| Feedar & Kloth healing (1985) Phys. Ther. | 8 | 3:control 5:treatment (stage IV decubitus ulcers) | high voltage short duration (60 microsec. pulses) | 3.7 | 7.3 | 25.3% per weekrate w/increased control would size |

FIELD OF THE INVENTION

The present invention relates generally to methods for treating soft tissue wounds, especially decubitus ulcers and more particularly to methods for accelerating healing of soft tissue wounds by electrical stimulation.

BACKGROUND OF THE INVENTION

It is well-know that immobilized persons experience skin ulcerations, or pressure sores, which occur when the skin is subjected to external pressure for prolonged periods. The increased tissue pressure results in reduced oxygen delivery to the tissue and ultimately to the development of ulcers in the muscle, skin and connective tissue. Ischemic skin ulcers also result from chronic venous stasis,. peripheral arterial insufficiency (as in diabetics), certain infections, venomous bites, sickle cell anemia, and numerous other pathophysiologic and physical factors.

Conventional methods for treating soft tissue wounds include applications of various ointments or medicaments to aid the natural body healing process. Another method is to relieve the pressure which caused the sore. A variety of mattresses, beds, wheelchair cushions and other pads have been devised to reduce pressure or distribute pressure more evenly over the body. However, it has been found that some wounds, including chronic wounds, do not respond to conventional treatment methods and resist healing.

It has been reported in the literature that healing of soft tissue wounds can be accelerated through use of electrical stimulation. Some researches have reported beneficial and reproducible healing when other treatment methods have failed. The result of some prior studies are summarized in Table 1 below:

Electrical stimulation is generally applied by the use of two electrodes, referred to as the active electrode and the dispersive electrode. The active electrode is usually applied directly over the soft tissue wound, or is immersed in a saline solution into which the body part is also placed. In either case, the dispersive electrode, or return electrode, is positioned in contact with the body of the patient as far as possible from the wound.

Prior methods of treatment using electrical stimulation have several disadvantages. First, prior treatment methods call for application of an electrical stimulation to the patient's body over long periods of time. Most of these prior art treatment methods call for current being applied over periods from between thirty minutes to several hours. Since most patients will have more than one sore, the prior art methods are not very practical due to the time it takes to treat each sore.

Another drawback of prior art methods is that some patients have experienced pain during application of the electrical stimulation. The pain is caused by an acid or base buildup on the electrodes used to apply the electrical stimulation to the patient's body. These acid and base buildups can burn the patient's skin and cause the treatment to be very painful.

Also, past treatment methods have utilized electrodes having relatively large surface areas which are applied directly over the sore by direct pad application. The direct pad application to the sore is a source for bacterial contamination which can complicate treatment of the sore.

SUMMARY AND OBJECTS OF THE INVENTION

The present invention provides an improved process for promoting and accelerating healing of soft tissue wounds using electrical stimulation. The process of the present invention involves application of electrical pulses having a substantially rectangular waveform and which reverses polarity at a relatively high frequency. Current is applied by two electrodes disposed closely adjacent to and on opposite sides of the wound so that the path of the current is across the wound. The current is applied in predetermined intervals and the electrodes are repositioned at predetermined incremental positions after each interval until the entire area of the wound has been covered. The probes are preferably formed from cotton swabs saturated in a zinc oxide solution. During application of the electrical current to the patient's body, the zinc is incorporated into body tissues by iontophoresis. The zinc ions incorporated into the cells promote the healing process and increases the tensile strength of the new tissue.

Accordingly, it is a primary object of the present invention to provide an improved process for promoting and accelerating the healing of soft tissue wounds.

Another object of the present invention is to provide an improved process for enhancing soft tissue wound healing by electrical stimulation.

Still another object of the present invention is to provide a process for enhancing soft tissue wound healing by zinc iontophoresis.

Another object of the present invention resides in the provision of a method or process for treating decubitus ulcers by providing direct electrical stimulation to the ulcer itself.

Other objects and advantages of the present invention will become apparent and obvious from a study of the following description and the accompanying drawings which are merely illustrative of such invention.

DETAILED DESCRIPTION OF THE INVENTION

Figure 2:
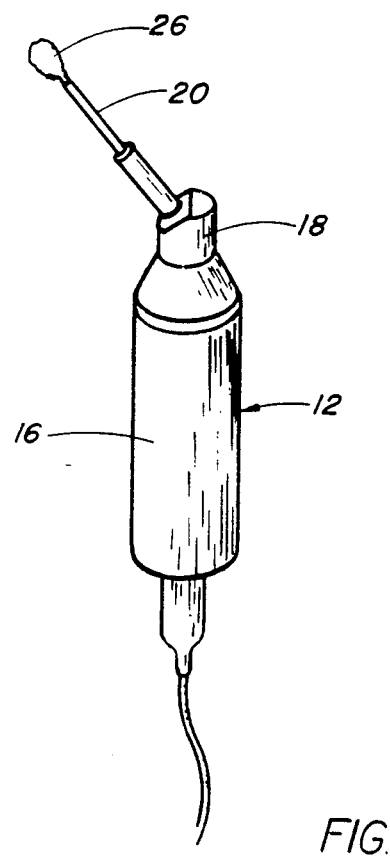
FIG. 2 is a perspective view of a probe used to apply the current to the patient's body.
Figure 1:
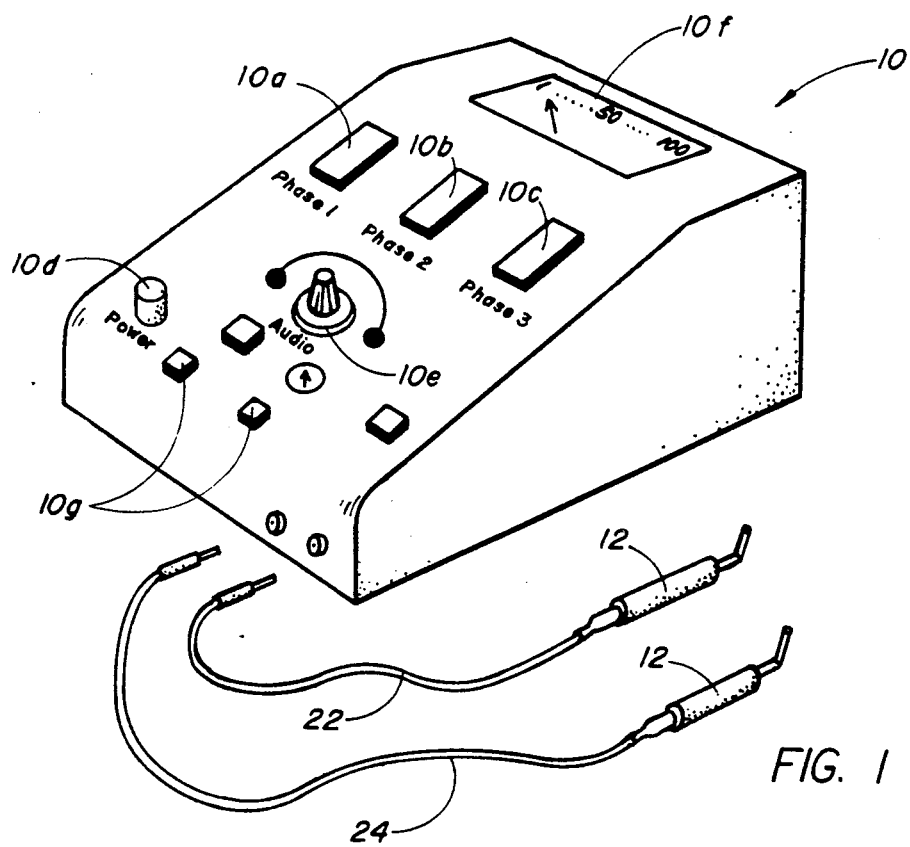
FIG. 1 is a perspective view of a current generator used in the treatment method of the present invention.

Referring now to the drawings, the method and apparatus for treatment of soft tissue wounds is shown. The method of the present invention involves the electrical stimulation of the healing process by the application of an applied DC current. DC current is generated by a current generator indicated generally at 10, and is applied to the patient's body through a pair of probes indicated at 12 which are positioned adjacent to the soft tissue wound. Contrary to the teachings of the prior art, direct application of the probes 12 to the wound by means of direct pad application, or through hydrotherapy, is avoided.

The current generator 10 has three phase switches 10a, 10b and 10c. Actuation of any one of the phase switches automatically deactuates the other switches so that only one switch can be actuated at any given time. The current generator 10 also includes a power switch 10d, and a volume control knob 10e. In its preferred form, the current generator 10 will produce an audible tone whenever it is being used and the tone will differ depending upon which of the phase switches is actuated. This audio feedback will serve to remind the therapist of the current setting of the current generator. The volume of the audio feedback is controlled by knob 10e. The current generator may also, but not necessarily, include a current meter 10f to indicate the current being applied and polarity indicators 10g which consists of two lights which alternately switch on and off each time the polarity of the generated current changes. These additional features provide means for the therapist to confirm that the generator is in proper working order.

The current generator 10 produces an output current with a modified square DC biphasic Pulses. The current generator 10 is capable of providing frequencies of 1 to 100 pulses per second. In addition, the current generator delivers a current of between 40 to 320 microamperes with a peak output voltage of 18 volts. The current generator has three settings corresponding to the phase switches 10a, 10b, and 10c, each of which produces a different waveform.

Figure 3:
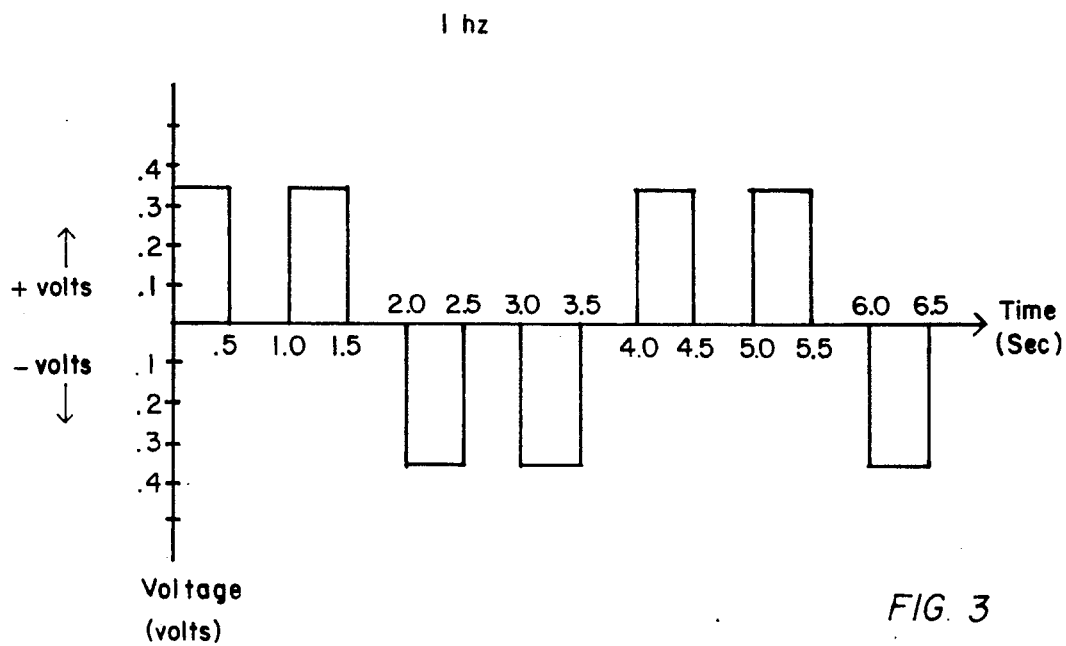
FIGS. 3-5 are typical waveforms representing the current produced by the current generator at three different settings.
Figure 4:
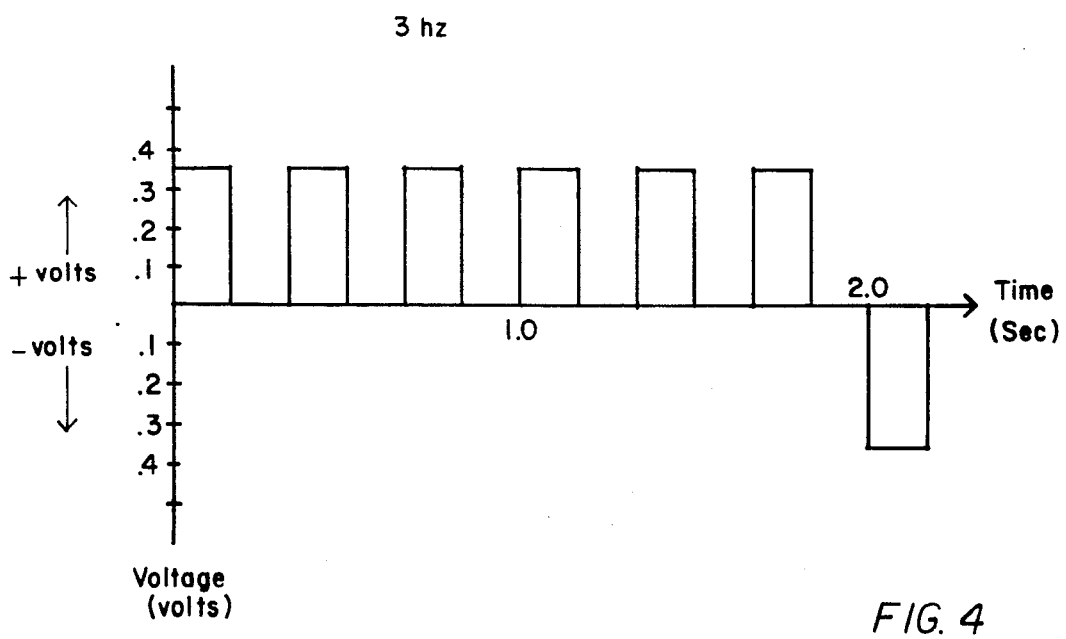
Figure 5:
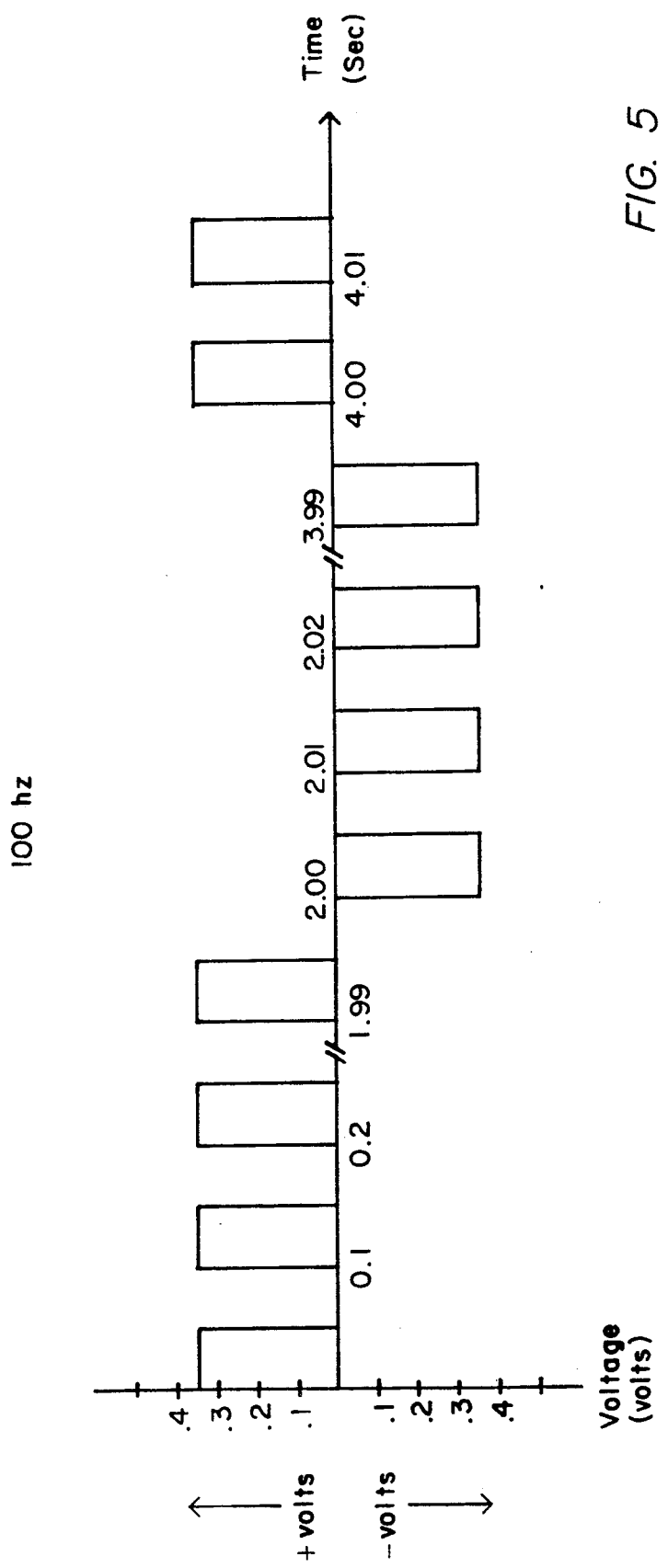
Figure 6:
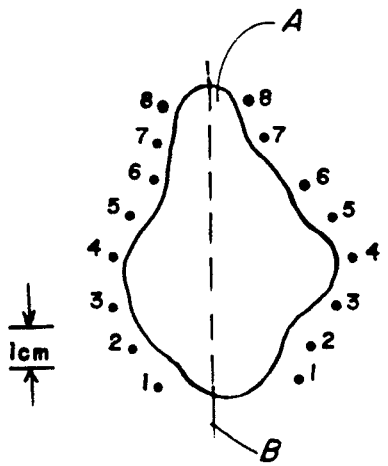
FIG. 6 is a diagram illustrating the first phase of the treatment method.
Figure 7:
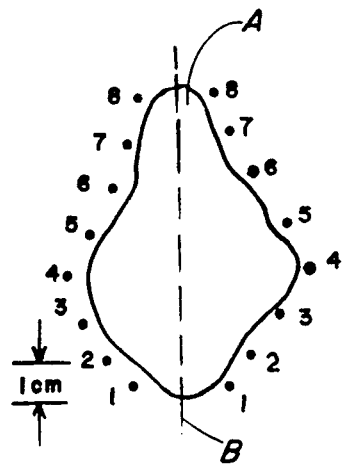
FIG. 7 is a diagram illustrating a first step of the second phase of the treatment method.

FIGS. 3-5 show the waveforms produced by the current generator across a 10 k ohm load. FIG. 3 shows the waveform produced at the first setting, FIG. 4 shows the waveform produced at the second setting, and FIG. 5 shows the waveform produced at the third setting.

Referring now to FIG. 3, there is shown a graph of a typical waveform generated by the current generator at the first setting. This waveform has a frequency of one pulse per second and an amplitude of approximately 0.35±volts. The polarity of the waveform is reversed every two seconds. The current intensity of the waveform is 40 microamperes.

The waveform shown in FIG. 4 is produced by the current generator at the second setting. At this setting, the current generator 10 produces rectangular pulses at a rate of three pulses per second with an amplitude of approximately 0.4+/−volts. As with the first setting, polarity is reversed every two seconds. The current intensity remains at 40 amperes.

Referring to FIG. 5, the waveform produced by the current generator at a third setting is shown. At this setting, the current generator 10 produces rectangular pulses at the rate of 100 pulses per second with a current intensity of 320 microamperes. The amplitude of the waveform is approximately 0.4±volts. Again, the current reverses polarity every two seconds.

The current from the current generator 10 is applied to the patient's body by two probes 12. Each of the probes consists of a handle portion 16 made of an insulating material, and head portion 18, and a probe tip 20 which screws into the head portion 18. Thus, the probe tip 20 can be removed for cleaning and sterilization. The probes 12 are connected to the current generator 10 by wires 22 and 24.

In use, cotton swabs 26 are wetted with an electrolyte solution and inserted into the probe tips 20. After each treatment, the swabs 26 are disposed of and new swabs 26 are inserted before treating the next patient.

FIGS. 6 through 9 illustrate a typical treatment cycle for soft tissue wound treatment. Prior to such treatment, the wound A and surrounding area should be thoroughly cleaned with a saline solution. The probes 12 of the current generator 10 should be cleaned with alcohol. After cleaning the probes, the cotton swabs 26 are inserted into the probes. The tips of the cotton swabs are then dipped in an electrolyte solution which preferably is a zinc oxide solution.

During a first phase of the treatment process, the probes 12 are placed closely adjacent the outer boundaries of the sore and on laterally opposite sides of the sore. For purposes of this application, the term "laterally opposite" shall mean placement on opposite sides of the wound along a line perpendicular to an imaginary line B which generally bi-sects the wound. The probes are held in place at a first position at one end of the sore for approximately ten seconds to apply an electrical current to the patient's body. During this initial phase, the current generator 10 should be set at the first setting. After ten seconds, the probes are moved up or down the sides of the sore at approximately one centimeter increments. At each stop, the probes are held in place approximately ten seconds while the current is applied. This process is repeated as many times as necessary to cover the entire length of the sore. This step is shown diagramatically in FIG. 6.

After completing the first phase of the treatment, the current generator is set on its second setting so as to produce a 40 microamp, 3 Hz waveform. During a first step of the second phase of the treatment, the probes are placed closely adjacent the outer boundaries of the wound and on laterally opposite sides of the wound as previously described. The probes are moved in one centimeter increments and held in place approximately ten seconds at each stop until the entire length of the wound has been covered. This step is illustrated diagramatically in FIG. 7.

Figure 8:
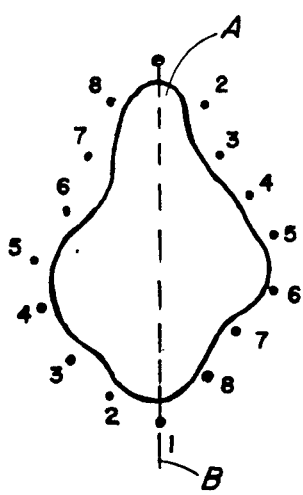
FIG. 8 is a diagram illustrating a second step of the second phase of the treatment method.

For the second step of the second phase of the treatment cycle shown diagramatically in FIG. 8, the current generator 10 is maintained at the second setting. The probes are placed on "diametrically opposite" sides of the sore. For purposes of this application, the term "diametrically opposite" shall mean on opposite sides of the sore along a line extending through the approximate center of the sore. The probes are held in place for approximately ten seconds and are then moved in approximately twelve to twenty-four degree increments, depending on the size of the sore, until the entire sore has been circumscribed. Since larger sores have greater surface area, smaller increments should be used than for smaller sores. At each stop, the probes are held in place for approximately ten seconds while the current is applied. Once the sore has been circumscribed, the second phase of the treatment cycle is completed.

Figure 9:
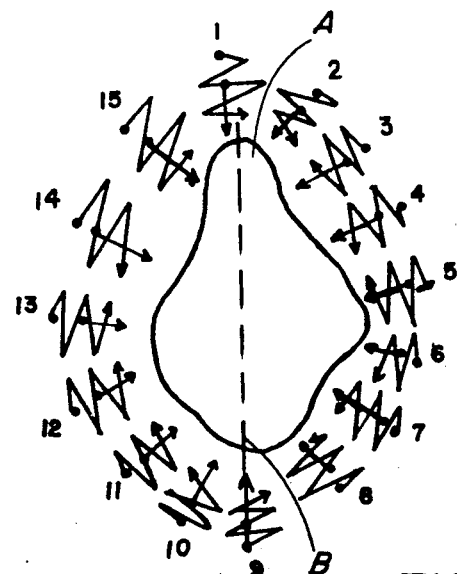
FIG. 9 is a diagram illustrating the third and final phase of the treatment method.

For the third phase of the treatment process, shown diagramatically in FIG. 9, the current generator 10 is set on the third setting which produces a 320 microamp current with a pulse rate of 100 pulses per second. During the third phase, the current is applied in a wide area surrounding the sore in order to stimulate blood supply to this area to prevent enlargement of the sore. Another function of the third phase is to promote assimilation of zinc ions into the body tissue by iontophoresis. Zinc has been reported to be necessary for active growth and repair of tissue. Some investigators have thought that zinc promotes resynthesis of protein and nucleic acids at the wound site by incorporating itself into certain enzyme systems The zinc ion, when introduced into body tissues by iontophoresis, has also been documented to have anti-bacterial effect.

Referring now to FIG. 9, the final phase of the treatment process is illustrated. The probes are placed side-by-side approximately five to six inches from the outer boundary of the sore. A first one of the probes is moved slowly in a straight line towards the sore and is followed by the other probe which is moved in a zigzag fashion towards the sore. During this brushing procedure, the current is applied to the skin to stimulate blood flow and effect zinc iontophoresis. This process is repeated as many times as necessary to circumscribe the wound.

The procedures described above were developed empirically over many years during which a variety of procedures and protocols were attempted. It is appreciated by the inventors that these protocols are not essential and that beneficial results can be achieved using various other protocols. However, the inventors believe that the protocols set forth herein produce the best results of those protocols attempted by the inventors.

The method of the present invention stimulates the healing process and can achieve very beneficial results even when other conventional treatment methods have failed. Nevertheless, the precise mechanism by which the healing process is stimulated is not fully understood. A number of natural processes might be involved.

There is evidence that injured tissue, especially involving an open wound, will have a naturally occuring wound current. There is a total voltage difference of 30 to 80 millivolts across the epidermis due to the cumulative effect of small differences in the transmembrane voltage in different regions of each keratinocyte cell. If the integrity of the epidural tissue is broken by a wound, there will be a net flow of ionic current through the low resistance pathway of the injured cells. It is hypothesized that the current flow pattern between normal and insulted tissue plays an important role in stimulating membrane repair processes that are essential to the restoration of the tissue to a normal and healthy state. It follows logically that the rates at which these processes occur may be accelerated by use of a stimulating current which passes through the insulted tissue.

One mechanism that might be involved is the opening of voltage sensitive ion channels (especially calcium channels) in the plasma membrane. The flow of electrical current across the plasma membrane will result in a voltage drop across that membrane. The change in the transmembrane voltage would be expected to effect the permeability of any voltage sensitive ion channels that exist in the membrane.

The flow of electrical current through epidural has also been observed to stimulate the production of adenosine triphosphate (ATP), a required energy source for many intracellular biochemical processes. Cellular physiologists now recognize that stimuli which activate most energy requiring processes within cells do so via an increase in intracellular calcium.

Electrical current from an external source has also been found to stimulate protein synthesis. It is known that tissue cells synthesize a very large number of specific types of protein molecules, both to sustain the normal functional processes, and to repair damaged tissue.

Another factor which contributes to the healing process is the increased blood flow to the area surrounding the ulcer brought about by electrical stimulation. The increased blood flow should mitigate the ischemic conditions which caused the sores.

Whatever the mechanism, the method of the present invention is beneficial in the treatment of soft tissue wounds and is known to promote healing even when standard methods have failed. The process has practical utility for use in both homes and hospitals since the current generator is of small size and is easily portable. Further, the equipment and the protocols are relatively simple and any reasonably capable individual should be capable of using the described treatment method disclosed herein.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended Claims are intended to be embraced therein.

What is claimed is:

1. A method for treating pressure sores and other soft tissue wounds in a patient's skin tissue comprising:
   (a) positioning a pair of electrodes in contact with the patient's skin tissue closely adjacent to and on opposite sides of the soft tissue wound;
   (b) applying a pulsed DC current of predetermined intensity to the patient's skin through the electrodes on opposite sides of the wound for a predetermined time interval so that the current flowing between the electrodes crosses over the soft tissue wound; and
   (c) brushing a wide area of the patient's skin tissue surrounding the soft tissue wound with at least one of the electrodes to increase blood circulation to the skin tissue surrounding the soft tissue wound.

2. The method according to claim 1 wherein the electrodes are positioned on laterally opposite sides of the wound.

3. The method according to claim 1 wherein the electrodes are positioned on diametrically opposite sides of the wound.

4. The method according to claim 1 wherein the electrodes are placed on laterally opposite sides of the wound during a first treatment phase and on diametrically opposite sides of the wound during a second treatment phase.

5. The method according to claim 1 wherein the current has an intensity of approximately 40 microamperes.

6. The method according to claim 1 wherein the pulsed DC current has a frequency of approximately 1 hz.

7. The method according to claim 1 wherein the pulsed DC current has a frequency of approximately 3 hz.

8. The method according to claim 1 further including the step of reversing the polarity of the DC current at predetermined intervals of short duration to prevent acid and base build-up on the electrodes.

9. The method according to claim 1 wherein the current is applied for a short duration each time the electrodes are positioned or repositioned.

10. The method according to claim 9 wherein the current is applied in intervals of 10–60 seconds.

11. A method for treating pressure sores and other soft tissue wounds, in a patient's skin tissue comprising:
   (a) attaching pads made of an absorbent material to a pair of electrodes;
   (b) saturating the pads with a zinc oxide solution;
   (c) positioning the electrodes closely adjacent to the soft tissue wound with the electrodes on opposite sides of the wound;
   (d) applying a pulsed DC current of predetermined intensity to the patient's skin tissue through the electrodes for a predetermined time interval of relatively short duration so that the current flowing between the electrodes crosses directly over the soft tissue wound to stimulate the healing of the soft tissue wound and to effect iontophoresis of zinc into the tissue adjacent the soft tissue wound; and
   (e) reversing the direction of current flow at a relatively high rate while the current is being applied.

12. The method according to claim 11 wherein the electrodes are positioned on laterally opposite sides of the wound.

13. The method according to claim 11 wherein the electrodes are positioned on diametrically opposite sides of the wound.

14. The method according to claim 11 wherein the electrodes are placed on laterally opposite sides of the wound during a first treatment phase and on diametrically opposite sides of the wound during a second treatment phase.

15. The method according to claim 11 further including the step of brushing a wide area surrounding the soft tissue wound with at least one of the electrodes while the other of the electrodes is positioned adjacent the area being brushed to increase blood circulation to the tissue surrounding the soft tissue wound.

16. The method according to claim 11 wherein the current has an intensity of approximately 40 microamperes.

17. The method according to claim 11 wherein the pulsed DC current has a frequency of approximately 1 hz.

18. The method according to claim 11 wherein the pulsed DC current has a frequency of approximately 3 hz.

* * * * *